United States Patent
Blank

(10) Patent No.: US 6,333,398 B1
(45) Date of Patent: *Dec. 25, 2001

(54) PROTEIN PURIFICATION

(75) Inventor: Gregory S. Blank, Menlo Park, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/587,820

(22) Filed: Jun. 6, 2000

Related U.S. Application Data

(63) Continuation of application No. 08/995,048, filed on Nov. 20, 1997, now Pat. No. 6,127,526.
(60) Provisional application No. 60/031,500, filed on Nov. 27, 1996.

(51) Int. Cl.[7] .................................................. C07K 1/22
(52) U.S. Cl. ........................................ 530/413; 530/387.3
(58) Field of Search ................................ 530/413, 387.3

(56) References Cited

U.S. PATENT DOCUMENTS

| | | | |
|---|---|---|---|
| 5,200,471 | 4/1993 | Coleman et al. | 525/326.9 |
| 5,429,746 | 7/1995 | Shadle et al. | 210/635 |
| 5,451,660 | 9/1995 | Builder et al. | 530/344 |
| 5,731,168 | 3/1998 | Carter et al. | 435/69.1 |
| 6,127,526 | * 10/2000 | Blank | 530/413 |

FOREIGN PATENT DOCUMENTS

| | | |
|---|---|---|
| 263934 | 4/1988 | (EP). |
| 323027 | 7/1989 | (EP). |
| 5262799 | 10/1993 | (JP). |
| WO 94/07912 | 4/1994 | (WO). |

OTHER PUBLICATIONS

Carter et al., "Humanization of an anti–p185$^{HER2}$ antibody for human cancer therapy" *Proc. Natl. Acad. Sci.* 89:4285–4289 (May 1992).

Chamow et al., "A Humanized, Bispecific Immunoadhesin–Antibody That Retargets CD3$^+$Effectors to kill HIV–1–Infected Cells" *Journal of Immunology* 153:4268–4280 (1994).

Mark et al., "Expression and Characterization of Hepatocyte Growth Factor Receptor–IgG Fusion Proteins" *The Journal of Biological Chemistry* 267 (36):26166–26171 (Dec. 25, 1992).

Sulkowski, E et al., "Controlled Pore Glass Chromatography of Proteins" *Protein Purification: Micro to Macro: proceedings of a Cetus–UCLA symposium* (Frisco, Colorado, Mar. 20–Apr. 4, 1987) Richard Burgess, New York:A.R. Liss vol. 68:177–195 (1987).

Dean, John A. *Lang's Handbook of Chemistry*. 13th edition. New York:McGraw–Hill Book Company pp. 7–627 and 7–634 (1986).

Tanford, Charles *The Hydrophobic Effect: Formation of Michelles and Biological Membranes*. New York:John Wiley & Sons pp. 1 (1980).

* cited by examiner

*Primary Examiner*—David Saunders
(74) *Attorney, Agent, or Firm*—Wendy M. Lee

(57) ABSTRACT

A method for purifying proteins by Protein A chromatography is described which comprises the steps of: (a) adsorbing the protein to Protein A immobilized on a solid phase comprising silica or glass; (b) removing contaminants bound to the solid phase by washing the solid phase with a hydrophobic electrolyte solvent; and (c) recovering the protein from the solid phase.

15 Claims, No Drawings

PROTEIN PURIFICATION

This is a continuation of application Ser. No. 08/995,048 filed Nov. 20, 1997 (now U.S. Pat. No. 6,127,526 issued Oct. 3, 2000), which is a non-provisional application filed under 37 CFR 1.53(b) (1), claiming priority under USC Section 119(e) to provisional Application Serial No. 60/031,500, filed on Nov. 27, 1996, both disclosures of which are hereby incorporated by reference.

BACKGROUND OF THE INVENTION

1. Field of the Invention

This invention relates generally to protein purification. In particular, the invention relates to a method for purifying $C_H2/C_H3$ region-containing proteins, such as antibodies and immunoadhesins, by Protein A affinity chromatography.

2. Description of Related Art

The large-scale, economic purification of proteins is increasingly an important problem for the biotechnology industry. Generally, proteins are produced by cell culture, using either mammalian or bacterial cell lines engineered to produce the protein of interest by insertion of a recombinant plasmid containing the gene for that protein. Since the cell lines used are living organisms, they must be fed with a complex growth medium, containing sugars, amino acids, and growth factors, usually supplied from preparations of animal serum. Separation of the desired protein from the mixture of compounds fed to the cells and from the by-products of the cells themselves to a purity sufficient for use as a human therapeutic poses a formidable challenge.

Procedures for purification of proteins from cell debris initially depend on the site of expression of the protein. Some proteins can be caused to be secreted directly from the cell into the surrounding growth media; others are made intracellularly. For the latter proteins, the first step of a purification process involves lysis of the cell, which can be done by a variety of methods, including mechanical shear, osmotic shock, or enzymatic treatments. Such disruption releases the entire contents of the cell into the homogenate, and in addition produces subcellular fragments that are difficult to remove due to their small size. These are generally removed by differential centrifugation or by filtration. The same problem arises, although on a smaller scale, with directly secreted proteins due to the natural death of cells and release of intracellular host cell proteins in the course of the protein production run.

Once a clarified solution containing the protein of interest has been obtained, its separation from the other proteins produced by the cell is usually attempted using a combination of different chromatography techniques. These techniques separate mixtures of proteins on the basis of their charge, degree of hydrophobicity, or size. Several different chromatography resins are available for each of these techniques, allowing accurate tailoring of the purification scheme to the particular protein involved. The essence of each of these separation methods is that proteins can be caused either to move at different rates down a long column, achieving a physical separation that increases as they pass further down the column, or to adhere selectively to the separation medium, being then differentially eluted by different solvents. In some cases, the desired protein is separated from impurities when the impurities specifically adhere to the column, and the protein of interest does not, that is, the protein of interest is present in the "flow-through."

Affinity chromatography, which exploits a specific interaction between the protein to be purified and an immobilized capture agent, may also be an option for some proteins. Protein A is a useful adsorbent for affinity chromatography of proteins, such as antibodies, which contain an Fc region. Protein A is a 41 kD cell wall protein from *Staphylococcus aureas* which binds with a high affinity (about $10^{-8}$M to human IgG) to the Fc region of antibodies.

SUMMARY OF THE INVENTION

A problem associated with Protein A chromatography of contaminated protein preparations has been identified herein. In particular, it has been observed that in Protein A chromatography using a glass or silica surface for adsorbing the Protein A (e.g. where the Protein A is immobilized on a controlled pore glass column or a silicic acid column), contaminants in the protein preparation (such as Chinese Hamster Ovary proteins (CHOP), where the protein preparation is derived from a CHO cell) adhere to the glass or silica surface of the solid phase. This was found to occur even when the solid phase is coated with a reagent (such as glycerol) in an attempt to prevent nonspecific adherence thereto. An intermediate wash step has been devised herein which addresses this problem. This wash step serves to remove the contaminants, but not the immobilized Protein A or the protein of interest bound to the Protein A, from the solid phase. In particular, it has been found that hydrophobic electrolytes, e.g., tetramethylammonium chloride (TMAC) and tetraethylammonium chloride (TEAC), can be used in this intermediate wash step.

Accordingly, the invention provides a method for purifying a protein, which comprises a $C_H2/C_H3$ region, from a contaminated solution thereof by Protein A chromatography comprising the following steps performed sequentially: (a) adsorbing the protein to Protein A immobilized on a solid phase comprising silica or glass; (b) removing contaminants bound to the solid phase by washing the solid phase with a hydrophobic electrolyte solvent; and (c) recovering the protein from the solid phase.

In preferred embodiments, the protein is an antibody (e.g. an anti-HER2, anti-IgE or anti-CD20 antibody) or an immunoadhesin (e.g. a TNF receptor immunoadhesin).

DETAILED DESCRIPTION OF THE PREFERRED EMBODIMENTS

Definitions

When used herein, the term "Protein A" encompasses Protein A recovered from a native source thereof, Protein A produced synthetically (e.g. by peptide synthesis or by recombinant techniques), and variants thereof which retain the ability to bind proteins which have a $C_H2/C_H3$ region. Protein A can be purchased commercially from Repligen, Pharmacia and Fermatech.

The Protein A is immobilized on a solid phase. By "solid phase" is meant a non-aqueous matrix to which the Protein A can adhere. The solid phase of interest herein is one which comprises a glass or silica surface. The solid phase may be a purification column or a discontinuous phase of discrete particles. In preferred embodiments, the solid phase is a controlled pore glass column or a silicic acid column. In certain embodiments, the solid phase is coated with a reagent (such as glycerol) which is intended to prevent nonspecific adherence of contaminants to the solid phase.

The protein of interest herein is one which comprises a $C_H2/C_H3$ region and therefore is amenable to purification by Protein A chromatography. The term "$C_H2/C_H3$ region" when used herein refers to those amino acid residues in the Fc region of an immunoglobulin molecule which interact with Protein A. In preferred embodiments, the $C_H2/C_H3$ region comprises an intact $C_H2$ region followed by an intact $C_H3$ region, and most preferably comprises a Fc region of an immunoglobulin. Examples of $C_H2/C_H3$ region-containing proteins include antibodies, immunoadhesins and fusion proteins comprising a protein of interest fused to, or conjugated with, a $C_H2/C_H3$ region.

The "intermediate wash step" is a step performed after the protein of interest is loaded on the solid phase and adsorbed to the Protein A, but before the protein is recovered from the column. The intermediate wash step serves to remove contaminants nonspecifically bound to the solid phase, without significantly eluting the protein of interest from the solid phase. In the intermediate wash step, the solid phase is washed with a hydrophobic electrolyte solvent (e.g. the hydrophobic electrolyte solvent is passed through the Protein A column, where the solid phase is a column).

The "hydrophobic electrolyte solvent" in the intermediate wash step is that which is able to elute contaminants bound to the solid phase, without significantly eluting the immobilized Protein A or the protein of interest adsorbed thereto. Preferably the hydrophobic electrolyte solvent is an aqueous carrier (e.g. a buffer) comprising one or more hydrophobic electrolytes. Examples of hydrophobic electrolytes include the alkylamines; tetramethylammonium chloride TMAC), tetraethylammonium chloride (TEAC), tetrapropylammonium chloride and tetrabutylammonium chloride.

A "buffer" is a buffered solution that resists changes in pH by the action of its acid-base conjugate components. The "equilibration buffer" herein is that used to prepare the solid phase (with immobilized Protein A) for loading the protein of interest. The equilibration buffer is preferably isotonic and commonly has a pH in the range from about 6 to about 8. The equilibration buffer of the example was 25 mM Tris, 25 mM NaCl, 5 mM EDTA, pH 7.1. The "loading buffer" is that which is used to load the mixture of the $C_H2/C_H3$ region-containing protein and contaminants onto the solid phase to which the Protein A is immobilized. Often, the equilibration and loading buffers are the same. The "elution buffer" is used to elute the $C_H2/C_H3$ region-containing protein from the immobilized Protein A. Preferably the elution buffer has a low pH and thereby disrupts interactions between Protein A and the protein of interest. Preferably, the low pH elution buffer has a pH in the range from about 2 to about 5, most preferably in the range from about 3 to about 4. Examples of buffers that will control the pH within this range include phosphate, acetate, citrate and ammonium buffers, as well as combinations of these. The preferred such buffers are citrate and acetate buffers, most preferably sodium citrate or sodium acetate buffers. Other elution buffers are contemplated including high pH buffers (e.g. those having a pH of 9 or more) or buffers comprising a compound or composition such as $MgCl_2$ (2 mM) for eluting the protein of interest.

The term "antibody" is used in the broadest sense and specifically covers monoclonal antibodies (including full length monoclonal antibodies), polyclonal antibodies, multispecific antibodies (e.g., bispecific antibodies), and antibody fragments so long as they retain, or are modified to comprise, a $C_H2/C_H3$ region as herein defined.

"Antibody fragments" comprise a portion of a full length antibody, generally the antigen binding or variable region thereof . Examples of antibody fragments include Fab, Fab'F(ab')$_2$, and Fv fragments; single-chain antibody molecules; diabodies; linear antibodies; and multispecific antibodies formed from antibody fragments.

The term "monoclonal antibody" as used herein refers to an antibody obtained from a population of substantially homogeneous antibodies, i.e., the individual antibodies comprising the population are identical except for possible naturally occurring mutations that may be present in minor amounts. Monoclonal antibodies are highly specific, being directed against a single antigenic site. Furthermore, in contrast to conventional (polyclonal) antibody preparations which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al., Nature 256:495 (1975), or may be made by recombinant DNA methods (see, e.g., U.S. Pat. No. 4,816,567). The "monoclonal antibodies" may also be isolated from phage antibody libraries using the techniques described in Clackson et al, Nature 352:624–628 (1991) and Marks et al., J. Mol. Biol. 222:581–597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; and Morrison et al., Proc. Natl. Acad. Sci. USA 81:6851–6855 (1984)).

The term "hypervariable region" when used herein refers to the amino acid residues of an antibody which are responsible for antigen-binding. The hypervariable region comprises amino acid residues from a "complementarity determining region" or "CDR" (i.e. residues 24–34 (L1), 50–56 (L2) and 89–97 (L3) in the light chain variable domain and 31–35 (H1), 50–65 (H2) and 95–102 (H3) in the heavy chain variable domain; Kabat et al., Sequences of Proteins of Immunological Interest, 5th Ed. Public Health Service, National Institutes of Health, Bethesda, Md. (1991)) and/or those residues from a "hypervariable loop" (i.e. residues 26–32 (L1), 50–52 (L2) and 91–96 (L3) in the light variable domain and 26–32 (H1), 53–55 (H2) and 96–101 (H3) in the heavy chain variable domain; Chothia and Lesk J. Mol. Biol. 196:901–917 (1987)). "Framework" or "FR" residues are those variable domain residues other than the hypervariable region residues as herein defined.

"Humanized" forms of non-human (e.g., murine) antibodies are chimeric antibodies which contain minimal sequence derived from non-human immunoglobulin. For the most part, humanized antibodies are human immunoglobulins (recipient antibody) in which hypervariable region residues of the recipient are replaced by hypervariable region residues from a non-human species (donor antibody) such as mouse, rat, rabbit or nonhuman primate having the desired specificity, affinity, and capacity. In some instances, Fv framework region (FR) residues of the human immunoglobulin are replaced by corresponding non-human residues. Furthermore, humanized antibodies may comprise residues which are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FR regions are those of a human immunoglobulin sequence. The humanized antibody optionally also will comprise at least a portion of an immunoglobulin constant region (Fc), typically that of a human immunoglobulin. For further details, see Jones et al., *Nature* 321:522–525 (1986); Riechmann et al, *Nature* 332:323–329 (1988); and Presta, *Curr. Op. Struct. Biol.* 2:593–596 (1992).

As used herein, the term "immunoadhesin" designates antibody-like molecules which combine the "binding domain" of a heterologous "adhesin" protein (e.g. a receptor, ligand or enzyme) with the effector functions of an immunoglobulin constant domain. Structurally, the immunoadhesins comprise a fusion of the adhesin amino acid sequence with the desired binding specificity which is other than the antigen recognition and binding site (antigen combining site) of an antibody (i.e. is "heterologous") and an immunoglobulin constant domain sequence. The immunoglobulin constant domain sequence in the immunoadhesin is preferably derived from γ1, γ2, or γ4 heavy chains since immunoadhesins comprising these regions can be purified by Protein A chromatography (Lindmark et al., *J. Immunol. Meth.* 62:1–13 (1983)).

The term "ligand binding domain" as used herein refers to any native cell-surface receptor or any region or derivative thereof retaining at least a qualitative ligand binding of a corresponding native receptor. In a specific embodiment, the receptor is from a cell-surface polypeptide having an extracellular domain which is homologous to a member of the immunoglobulin supergenefamily. Other receptors, which are not members of the immunoglobulin supergenefamily but are nonetheless specifically covered by this definition, are receptors for cytokines, and in particular receptors with tyrosine kinase activity (receptor tyrosine kinases), members of the hematopoietin and nerve growth factor receptor superfamilies, and cell adhesion molecules, e.g. (E-, L- and P-) selecting.

The term "receptor binding domain" is used to designate any native ligand for a receptor, including cell adhesion molecules, or any region or derivative of such native ligand retaining at least a qualitative receptor binding ability of a corresponding native ligand. This definition, among others, specifically includes binding sequences from ligands for the above-mentioned receptors.

An "antibody-immunoadhesin chimera" comprises a molecule which combines at least one binding domain of an antibody (as herein defined) with at least one immunoadhesin (as defined in this application). Exemplary antibody-immunoadhesin chimeras are the bispecific CD4-IgG chimeras described in Berg et al., *PNAS* (USA) 88:4723–4727 (1991) and Chamow et al., *J. Immunol.* 153:4268 (1994).

Modes for Carrying Out the Invention

The process herein involves purifying a $C_H2/C_H3$ region-containing protein from contaminants by Protein A chromatography. In preferred embodiments, the protein to be purified using Protein A chromatography is an antibody, an immunoadhesin or a protein fused to, or conjugated with, a $C_H2/C_H3$ region. Techniques for generating such molecules will be discussed below.

1. Antibodies
    (i) Antigen Selection and Preparation
    The antibody herein is directed against an antigen of interest. Preferably, the antigen is a biologically important polypeptide and administration of the antibody to a mammal suffering from a disease or disorder can result in a therapeutic benefit in that mammal. However, antibodies directed against nonpolypeptide antigens (such as tumor-associated glycolipid antigens; see U.S. Pat. No. 5,091,178) are also contemplated. Where the antigen is a polypeptide, it may be a transmembrane molecule (e.g. receptor) or ligand such as a growth factor. Exemplary antigens include those proteins described in section (3) below. Preferred molecular targets for antibodies encompassed by the present invention include CD proteins such as CD3, CD4, CD8, CD19, CD20 and CD34; members of the ErbB receptor family such as the EGF receptor, HER2, HER3 or HER4 receptor; cell adhesion molecules such as LFA-1, Mac1, p150,95, VLA4, ICAM-1, VCAM and αv/β3 integrin including either α or β subunits thereof (e.g. anti-CD11a, anti-CD18 or anti-CD11b antibodies); growth factors such as VEGF; IgE; blood group antigens; flk2/flt3 receptor; obesity (OB) receptor; mpl receptor; CTLA-4; protein C etc.

Soluble antigens or fragments thereof, optionally conjugated to other molecules, can be used as immunogens for generating antibodies. For transmembrane molecules, such as receptors, fragments of these (e.g. the extracellular domain of a receptor) can be used as the immunogen. Alternatively, cells expressing the transmembrane molecule can be used as the immunogen. Such cells can be derived from a natural source (e.g. cancer cell lines) or may be cells which have been transformed by recombinant techniques to express the transmembrane molecule.

Other antigens and forms thereof useful for preparing antibodies will be apparent to those in the art.

(ii) Polyclonal Antibodies

Polyclonal antibodies are preferably raised in animals by multiple subcutaneous (sc) or intraperitoneal (ip) injections of the relevant antigen and an adjuvant. It may be useful to conjugate the antigen to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, $SOCl_2$, or $R^1N=C=NR$, where R and $R^1$ are different alkyl groups.

Animals are immunized against the antigen, immunogenic conjugates, or derivatives by combining, e.g., 100 μg or 5 μg of the protein or conjugate (for rabbits or mice, respectively) with 3 volumes of Freund's complete adjuvant and injecting the solution intradermally at multiple sites. One month later the animals are boosted with ⅕ to ¹/₁₀ the original amount of antigen or conjugate in Freund's complete adjuvant by subcutaneous injection at multiple sites. Seven to 14 days later the animals are bled and the serum is assayed for antibody titer. Animals are boosted until the titer plateaus. Preferably, the animal is boosted with the conjugate of the same antigen, but conjugated to a different protein and/or through a different cross-linking reagent. Conjugates also can be made in recombinant cell culture as protein fusions. Also, aggregating agents such as alum are suitably used to enhance the immune response.

(iii) Monoclonal Antibodies

Monoclonal antibodies may be made using the hybridoma method first described by Kohler et at., *Nature*, 256:495 (1975), or may be made by recombinant DNA methods (U.S. Pat. No. 4,816,567).

In the hybridoma method, a mouse or other appropriate host animal, such as a hamster or macaque monkey, is immunized as hereinabove described to elicit lymphocytes that produce or are capable of producing antibodies that will specifically bind to the protein used for immunization.

Alternatively, lymphocytes may be immunized in vitro. Lymphocytes then are fused with myeloma cells using a suitable fusing agent, such as polyethylene glycol, to form a hybridoma cell (Goding, *Monoclonal Antibodies: Principles and Practice*, pp.59–103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

Preferred myeloma cells are those that fuse efficiently, support stable high-level production of antibody by the selected antibody-producing cells, and are sensitive to a medium such as HAT medium. Among these, preferred myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, *J. Immunol.*, 133:3001 (1984); Brodeur et al., *Monoclonal Antibody Production Techniques and Applications*, pp. 51–63 (Marcel Dekker, Inc., New York, 1987)).

Culture medium in which hybridoma cells are growing is assayed for production of monoclonal antibodies directed against the antigen. Preferably, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

After hybridoma cells are identified that produce antibodies of the desired specificity, affinity, and/or activity, the clones may be subcloned by limiting dilution procedures and grown by standard methods (Goding, *Monoclonal Antibodies: Principles and Practice*, pp.59–103 (Academic Press, 1986)). Suitable culture media for this purpose include, for example, DMEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, Protein A SEPHAROSE™, hydroxylapatite chromatography, gel electrophoresis, dialysis, or affinity chromatography. Preferably the Protein A chromatography procedure described herein is used.

DNA encoding the monoclonal antibodies is readily isolated and sequenced using conventional procedures (e.g., by using oligonucleotide probes that are capable of binding specifically to genes encoding the heavy and light chains of the monoclonal antibodies). The hybridoma cells serve as a preferred source of such DNA. Once isolated, the DNA may be placed into expression vectors, which are then transfected into host cells such as E coli cells, simian COS cells, Chinese hamster ovary (CHO) cells, or myeloma cells that do not otherwise produce immunoglobulin protein, to obtain the synthesis of monoclonal antibodies in the recombinant host cells.

The DNA also may be modified, for example, by substituting the coding sequence for human heavy- and light-chain constant domains in place of the homologous murine sequences (U.S. Pat. No. 4,816,567; Morrison, et al., *Proc. Natl Acad. Sci.* USA, 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In a further embodiment, monoclonal antibodies can be isolated from antibody phage libraries generated using the techniques described in McCafferty et al., *Nature*, 348:552–554 (1990). Clackson et al., *Nature*, 352:624–628 (1991) and Marks et al., *J. Mol. Biol.*, 222:581–597 (1991) describe the isolation of murine and human antibodies, respectively, using phage libraries. Subsequent publications describe the production of high affinity (nM range) human antibodies by chain shuffling (Marks et al., *Bio/Technology*, 10:779–783 p1992)), as well as combinatorial infection and in vivo recombination as a strategy for constructing very large phage libraries (Waterhouse et al., *Nuc. Acids. Res.*, 21:2265–2266 (1993)). Thus, these techniques are viable alternatives to traditional hybridoma techniques for isolation of monoclonal antibodies.

(iv) Humanized and Human Antibodies

A humanized antibody has one or more amino acid residues introduced into it from a source which is non-human. These non-human amino acid residues are often referred to as "import" residues, which are typically taken from an "import" variable domain. Humanization can be essentially performed following the method of Winter and co-workers (Jones et al., *Nature*, 321:522–525 (1986); Riechmann et al., *Nature*, 332:323–327 (1988); Verhoeyen et al., *Science*, 239:1534–1536 (1988)), by substituting rodent CDRs or CDR sequences for the corresponding sequences of 10 a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some CDR residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence which is closest to that of the rodent is then accepted as the human FR for the humanized antibody (Sims et al., *J. Immunol.*, 151:2296 (1993)). Another method uses a particular framework derived from the consensus sequence of all human antibodies of a particular subgroup of light or heavy chains. The same framework may be used for several different humanized antibodies (Carter et al., *Proc. Natl. Acad. Sci.* USA, 89:4285 (1992); Presta et al., *J. Immnol.*, 151:2623 (1993)).

It is further important that antibodies be humanized with retention of high affinity for the antigen and other favorable biological properties. To achieve this goal, according to a preferred method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the CDR residues are directly and most substantially involved in influencing antigen binding.

Alternatively, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci.* USA, 90:2551 (1993); Jakobovits et al, *Nature*, 362:255–258 (1993); Bruggermann et al, *Year in Immuno.*, 7:33 (1993); and Duchosal et al *Nature* 355:258 (1992). Human antibodies can also be derived from phage-display libraries (Hoogenboom et al., *J. Mol. Biol.*, 227:381 (1991); Marks et al, *J. Mol. Biol.*, 15, 222:581–597 (1991); Vaughan et al. *Nature Biotech* 14:309 (1996)).

(v) Antibody Fragments

Various techniques have been developed for the production of antibody fragments. Traditionally, these fragments were derived via proteolytic digestion of intact antibodies (see, e.g., Morimoto et al. , *Journal of Biochemical and Biophysical Methods* 24:107–117 (1992) and Brennan et al., *Science*, 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10:163–167 (1992)). According to another approach, F(ab')$_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185.

(vi) Multispecific Antibodies

Multispecific antibodies have binding specificities for at least two different antigens. While such molecules normally will only bind two antigens (i.e. bispecific antibodies, BsAbs), antibodies with additional specificities such as trispecific antibodies are encompassed by this expression when used herein.

Methods for making bispecific antibodies are known in the art. Traditional production of full length bispecific antibodies is based on the coexpression of two immunoglobulin heavy chain-light chain pairs, where the two chains have different specificities (Millstein et al., *Nature*, 305:537–539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al, *EMBO J.*, 10:3655–3659 (1991).

According to another approach described in WO 96/27011, the interface between a pair of antibody molecules can be engineered to maximize the percentage of heterodimers which are recovered from recombinant cell culture. The preferred interface comprises at least a part of the $C_H3$ domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science*, 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Recent progress has facilitated the direct recovery of Fab'-SH fragments from *E. coli*, which can be chemically coupled to form bispecific antibodies. Shalaby et al., *J. Exp. Med.*, 175: 217–225 (1992) describe the production of a fully humanized bispecific antibody F(ab')$_2$ molecule. Each Fab' fragment was separately secreted from *E. coli* and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al.,*J.*

*Immunol.*, 148(5):1547–1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA*, 90:6444–6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (sFv) dimers has also been reported. See Gruber et al., *J. Immunol.*, 152:5368 (1994). Alternatively, the antibodies can be "linear antibodies" as described in Zapata et al. *Protein Eng.* 8(10):1057–1062 (1995). Briefly, these antibodies comprise a pair of tandem Fd segments ($V_H$-$C_H$1-$V_H$-$C_H$1) which form a pair of antigen binding regions. Linear antibodies can be bispecific or monospecific.

Antibodies with more than two valencies are contemplated. For example, trispecific antibodies can be prepared. Tutt et al. *J. Immunol.* 147: 60 (1991).

2. Immunoadhesins

The simplest and most straightforward immunoadhesin design combines the binding domain(s) of the adhesin (e.g. the extracellular domain (ECD) of a receptor) with the hinge and Fc regions of an immunoglobulin heavy chain. Ordinarily, when preparing the immunoadhesins of the present invention, nucleic add encoding the binding domain of the adhesin will be fused C-terminally to nucleic add encoding the N-terminus of an immunoglobulin constant domain sequence, however N-terminal fusions are also possible.

Typically, in such fusions the encoded chimeric polypeptide will retain at least functionally active hinge, $C_H2$ and $C_H3$ domains of the constant region of an immunoglobulin heavy chain. Fusions are also made to the C-terminus of the Fc portion of a constant domain, or immediately N-terminal to the $C_H1$ of the heavy chain or the corresponding region of the light chain. The precise site at which the fusion is made is not critical; particular sites are well known and may be selected in order to optimize the biological activity, secretion, or binding characteristics of the immunoadhesin.

In a preferred embodiment, the adhesin sequence is fused to the N-terminus of the Fc domain of immunoglobulin $G_1$ (IgG$_1$). It is possible to fuse the entire heavy chain constant region to the adhesin sequence. However, more preferably, a sequence beginning in the hinge region just upstream of the papain cleavage site which defines IgG Fc chemically (i.e. residue 216, taking the first residue of heavy chain constant region to be 114), or analogous sites of other immunoglobulins is used in the fusion. In a particularly preferred embodiment, the adhesin amino acid sequence is fused to (a) the hinge region and $C_H2$ and $C_H3$ or (b) the $C_H1$, hinge, $C_H2$ and $C_H3$ domains, of an IgG heavy chain.

For bispecific immunoadhesins, the immunoadhesins are assembled as multimers, and particularly as heterodimers or heterotetramers. Generally, these assembled immunoglobulins will have known unit structures. A basic four chain structural unit is the form in which IgG, IgD, and IgE exist. A four chain unit is repeated in the higher molecular weight immunoglobulins; IgM generally exists as a pentamer of four basic units held together by disulfide bonds. IgA globulin, and occasionally IgG globulin, may also exist in multimeric form in serum. In the case of multimer, each of the four units may be the same or different.

Various exemplary assembled immunoadhesins within the scope herein are schematically diagrammed below:

(a) $AC_L$-$AC_L$;
(b) $AC_H$-($AC_H$, $AC_L$-$AC_H$, $AC_L$-$V_H C_H$, or $V_L C_L$-$AC_H$);
(c) $AC_L$-$AC_H$-($AC_L$-$AC_H$, $AC_L$-$V_H C_H$, $V_L C_L$-$AC_H$, or $V_L C_L$-$V_H C_H$)
(d) $AC_L$-$V_H C_H$-($AC_H$, or $AC_L$-$V_H C_H$, or $V_L C_L$-$AC_H$);
(e) $V_L C_L$-$AC_H$-($AC_L$-$V_H C_H$, or $V_L C_L$-$AC_H$); and
(f) $(A\text{-}Y)_n$-$(V_L C_L\text{-}V_H C_H)_2$, wherein each A represents identical or different adhesin amino acid sequences;

$V_L$ is an immunoglobulin light chain variable domain;
$V_H$ is an immunoglobulin heavy chain variable domain;
$C_L$ is an immunoglobulin light chain constant domain;
$C_H$ is an immunoglobulin heavy chain constant domain;
n is an integer greater than 1;
Y designates the residue of a covalent cross-linking agent.

In the interests of brevity, the foregoing structures only show key features; they do not indicate joining (J) or other domains of the immunoglobulins, nor are disulfide bonds shown. However, where such domains are required for binding activity, they shall be constructed to be present in the ordinary locations which they occupy in the immunoglobulin molecules.

Alternatively, the adhesin sequences can be inserted between immunoglobulin heavy chain and light chain sequences, such that an immunoglobulin comprising a chimeric heavy chain is obtained. In this embodiment, the adhesin sequences are fused to the 3' end of an immunoglobulin heavy chain in each arm of an immunoglobulin, either between the hinge and the $C_H2$ domain, or between the $C_H2$ and $C_H3$ domains. Similar constructs have been reported by Hoogenboom, et at., *Mol. Immunol.* 28:1027–1037 (1991).

Although the presence of an immunoglobulin light chain is not required in the immunoadhesins of the present invention, an immunoglobulin light chain might be present either covalently associated to an adhesin-immunoglobulin heavy chain fusion polypeptide, or directly fused to the adhesin. In the former case, DNA encoding an immunoglobulin light chain is typically coexpressed with the DNA encoding the adhesin-immunoglobulin heavy chain fusion protein. Upon secretion, the hybrid heavy chain and the light chain will be covalently associated to provide an immunoglobulin-like structure comprising two disulfide-linked immunoglobulin heavy chain-light chain pairs. Methods suitable for the preparation of such structures are, for example, disclosed in U.S. Pat. No. 4,816,567, issued Mar. 28, 1989.

Immunoadhesins are most conveniently constructed by fusing the cDNA sequence encoding the adhesin portion in-frame to an immunoglobulin cDNA sequence. However, fusion to genomic immunoglobulin fragments can also be used (see, e.g. Aruffo et al., *Cell* 61:1303–1313 (1990); and Stamenkovic et al., *Cell* 66:1133–1144 (1991)). The latter type of fusion requires the presence of Ig regulatory sequences for expression. cDNAs encoding IgG heavy-chain constant regions can be isolated based on published sequences from cDNA libraries derived from spleen or peripheral blood lymphocytes, by hybridization or by polymerase chain reaction (PCR) techniques. The cDNAs encoding the "adhesin" and the immunoglobulin parts of the immunoadhesin are inserted in tandem into a plasmid vector that directs efficient expression in the chosen host cells.

3. Other $C_H2/C_H3$ Region-containing Proteins

In other embodiments, the protein to be purified is one which is fused to, or conjugated with, a $C_H2/C_H3$ region. Such fusion proteins may be produced so as to increase the serum half-life of the protein and/or to facilitate purification of the protein by Protein A chromatography.

Examples of biologically important proteins which can be conjugated this way include renin; a growth hormone, including human growth hormone and bovine growth hormone; growth hormone releasing factor, parathyroid hormone; thyroid stimulating hormone; lipoproteins; alpha-1-antitrypsin; insulin A-chain; insulin B-chain; proinsulin; follicle stimulating hormone; calcitonin; luteinizing hormone; glucagon; dotting factors such as factor VIIIC, factor IX, tissue factor, and von Willebrands factor; anti-clotting factors such as Protein C; atrial natriuretic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; RANTES (regulated on activation normally T-cell expressed and secreted); human macrophage inflammatory protein (MIP-1-alpha); a serum albumin such as human serum albumin; Muellerian-inhibiting substance; relaxin A-chain; relaxin B-chain; prorelaxin; mouse gonadotropin-associated peptide; a microbial protein, such as beta-lactamase; DNase; IgE; a cytotoxic T-lymphocyte associated antigen (CTLA), such as CTLA4; inhibin; activin; vascular endothelial growth factor (VEGF); receptors for hormones or growth factors; Protein A or D; rheumatoid factors; a neurotrophic factor such as bone-derived neurotrophic factor (BDNF), neurotrophin-3, -4, -5, or -6 (NT-3, NT-4, NT-5, or NT-6), nerve growth factor such as NGF-β; platelet-derived growth factor (PDGF); fibroblast growth factor such as aFGF and bFGF; epidermal growth factor (EGF); transforming growth factor (TGF) such as TGF-alpha and TGF-beta, including TGF-β1, TGF-β2, TGF-β3, TGF-β4, or TGF-β5; insulin-like growth factor-I and-II (IGF-I and IGF-II); des(1–3)-IGF-I (brain IGF-I), insulin-like growth factor binding proteins; CD proteins such as CD3, CD4, CD8, CD19 and CD20; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; superoxide dismutase; T-cell receptors; surface membrane proteins; decay accelerating factor, viral antigen such as, for example, a portion of the AIDS envelope; transport proteins; homing receptors; addressing; regulatory proteins; integrins such as CD11a, CD11b, CD11c, CD18, an ICAM, VLA-4 and VCAM; a tumor associated antigen such as HER2, HER3 or HER4 receptor, and fragments of any of the above-listed polypeptides.

4. Protein Purification

The protein to be purified using the method described herein is generally produced using recombinant techniques. Methods for producing recombinant proteins are described, e.g., in U.S. Pat. No's. 5,534,615 and 4,816,567, specifically incorporated herein by reference. In preferred embodiments, the protein of interest is produced in a CHO cell (see, e.g. WO 94/11026). Examples of proteins which can be purified using the process described herein include humanized anti-HER2 antibody (WO92/22653); humanized anti-IgE antibody (Presta et al. *J. Immunol.* 151:2623–2632 (1993)); chimeric anti-CD20 antibody (WO94/11026); and TNF receptor immunoadhesin (Ashkenazi et al. *Proc. Natl. Acad. Sci* (USA) 88:10535–10539 (1991)).

When using recombinant techniques, the protein can be produced intracellularly, in the periplasmic space, or directly secreted into the medium. If the protein is produced intracellularly, as a first step, the particulate debris, either host cells or lysed fragments, is removed, for example, by centrifugation or ultrafiltration. Where the protein is secreted into the medium, the recombinant host cells may be separated from the cell culture medium by tangential flow filtration, for example.

Protein A immobilized on a solid phase is used to purify the $C_H2/C_H3$ region-containing protein. The solid phase is preferably a column comprising a glass or silica surface for immobilizing the Protein A. Preferably, the solid phase is a controlled pore glass column or a silicic acid column. Sometimes, the column has been coated with a reagent, such as glycerol, in an attempt to prevent nonspecific adherence to the column. The PROSEP A™ column, commercially available from Bioprocessing Limited, is an example of a Protein A controlled pore glass column which is coated with glycerol.

The solid phase for the Protein A chromatography is equilibrated with a suitable buffer. For example, the equilibration buffer may be 25 mM Tris, 25 mM NaCl, 5 mM EDTA, pH 7.1.

The contaminated preparation derived from the recombinant host cells is loaded on the equilibrated solid phase using a loading buffer which may be the same as the equilibration buffer. As the contaminated preparation flows through the solid phase, the protein is adsorbed to the immobilized Protein A and, as discovered herein, other contaminants (such as Chinese Hamster Ovary Proteins, CHOP, where the protein is produced in a CHO cell) bind nonspecifically to the solid phase.

The next step performed sequentially entails removing the contaminants bound to the solid phase by washing the solid phase with a hydrophobic electrolyte solvent in an intermediate wash step. In preferred embodiments, the hydrophobic electrolyte in this wash solvent is TMAC and/or TEAC. While a single hydrophobic electrolyte may be present in the wash solvent, in certain embodiments, two or more such electrolytes may be used. The hydrophobic electrolyte is preferably added to a pH buffered solution having a pH in the range from about 4 to about 8, and preferably in the range from about 5 to about 7. Suitable buffers for this purpose include Tris, phosphate, MES, and MOPSO buffers. The preferred final concentration for the hydrophobic electrolyte in the wash solvent is in the range from about 0.1 to about 1.0M, and preferably in the range from about 0.25 to about 0.5M.

Following the intermediate wash step of the preceding paragraph, the protein of interest is recovered from the column. This is normally achieved using a suitable elution buffer. The protein may, for example, be eluted from the column using an elution buffer having a low pH, e.g. in the range from about 2 to about 5, and preferably in the range from about 2.5 to about 3.5. Examples of elution buffers for this purpose include citrate or acetate buffers.

The eluted protein preparation may be subjected to additional purification steps either prior to, or after, the Protein A chromatography step. Exemplary further purification steps include hydroxylapatite chromatography; dialysis; affinity chromatography using an antibody to capture the protein; hydrophobic interaction chromatography (HIC); ammonium sulphate precipitation; anion or cation exchange chromatography; ethanol precipitation; reverse phase HPLC; chromatography on silica; chromatofocusing; and gel filtration.

The protein thus recovered may be formulated in a pharmaceutically acceptable carrier and is used for various diagnostic, therapeutic or other uses known for such molecules.

The following examples are offered by way of illustration and not by way of limitation. The disclosures of all citations in the specification are expressly incorporated herein by reference.

EXAMPLE 1

The PROSEP A™ column (Bioprocessing, Ltd) has Protein A immobilized on a glycerol coated-controlled pore glass column. The glycerol coating reduces the glass surface available for non-specific interactions with contaminants but, as demonstrated herein, contaminants can still adhere to the column.

Protein A chromatography was the initial chromatography step in the purification of the $C_H2/C_H3$ region-containing protein; humanized anti-HER2 antibody (humAb4D5-8) (Carter et al. *Proc. Natl. Acad. Sci.* 89: 4285–4289 (1992)). This anti-HER2 antibody was produced recombinantly in CHO cells. Following protein production and secretion to the cell culture medium, the CHO cells were separated from the cell culture medium by tangential flow filtration (PROSTACK™). In this expression system, the most prevalent contaminants were found to be Chinese Hamster Ovary Proteins (CHOP).

The PROSEP A™ column was equilibrated with 25 mM Tris, 25 mM NaCl, 5 mM EDTA, pH 7.1 (Buffer A). Protein A chromatography was performed by applying the Harvested Cell Culture Fluid (HCCF) from the CHO cells directly to the equilibrated PROSEP A™ column using Buffer A as the loading buffer. The column was then washed with Buffer A to wash out the HCCF and unbound proteins. The anti-HER2 antibody was eluted from the Protein A column by washing the column with Buffer B having a low pH (2.5–3.5). Buffer B was 25 mM sodium citrate, pH 2.8. The low pH of Buffer B disrupted the interactions between Protein A and the anti-HER2 antibody. It also disrupted the non-specific interactions between the exposed glass surfaces of the column and non-specifically bound contaminating CHOP. This resulted in a level of CHOP contamination in the eluted anti-HER2 containing protein pool of ~4000 ppm (Table 1).

TABLE 1[a]

| | | CHOP | |
|---|---|---|---|
| Sample | Conditions | (μg/ml) | (ppm) |
| HCCF | Load | 760 | 1,461,538 |
| Antibody Pool | No wash | 32 | 4,270 |
| Antibody Pool | TMAC, pH 5.0 wash | 3 | 408 |
| Antibody Pool | TEAC, pH 5.0 wash | 2 | 317 |
| Antibody Pool | TMAC, pH 7.1 wash | 4 | 537 |
| Antibody Pool | TEAC, pH 7.1 wash | 5 | 620 |

[a]The wash buffer was 25mM Tris, 25mM NaCl, 5mM EDTA including either 0.5M TMAC or TEAC at the indicated pH. Following the wash, the protein was eluted at pH 2.8.

In order to address this problem concerning contaminants in the eluted protein pool, an "intermediate wash step" was evaluated. Prior to eluting the antibody from the column, the Protein A column was washed with wash buffer (at varying pH's) to which various concentrations of TMAC or TEAC were added (Table 1).

As shown in Table 1, the intermediate wash step using a buffer containing either TMAC or TEAC was effective at lowering the level of CHOP in the eluted antibody pool. The concentration of either TMAC or TEAC was preferably at least 0.25M. Accordingly, it was found that preferred TMAC or TEAC concentrations in the wash solvent are from about 0.1 to about 1.0M, and preferably from about 0.25 to about 0.5M.

As to variations in the pH of the wash solution, it was found that the lower the pH, the greater removal of CHOP in the wash step. However, at pH's below 7.0, protein may also be partially eluted during the wash step. Therefore, preferred pH's for the intermediate wash step are from about 4 to about 8, and preferably from about 5 to about 7.

What is claimed is:

1. A method for purifying a protein, which comprises a $C_H2/C_H3$ region, from a contaminated solution thereof by Protein A chromatography comprising:

(a) adsorbing the protein to Protein A immobilized on a solid phase comprising silica or glass;

(b) removing contaminants bound to the solid phase by washing the solid phase with a hydrophobic electrolyte solvent; and (c) recovering the protein from the solid phase.

2. The method of claim 1 wherein the protein is an antibody.

3. The method of claim 1 wherein the protein is an immunoadhesin.

4. The method of claim 1 wherein a hydrophobic electrolyte in the hydrophobic electrolyte solvent comprises tetramethylammonium chloride (TMAC).

5. The method of claim 1 wherein a hydrophobic electrolyte in the hydrophobic electrolyte solvent comprises tetraethylammonium chloride (TEAC).

6. The method of claim 1 wherein the solid phase is a controlled pore glass column.

7. The method of claim 1 wherein the solid phase is a silicic acid column.

8. The method of claim 1 wherein the contaminants are Chinese Hamster Ovary Proteins (CHOP).

9. The method of claim 1 wherein the concentration of a hydrophobic electrolyte in the hydrophobic electrolyte solvent is in the range from about 0.1 to about 1.0 M.

10. The method of claim 1 wherein the pH of the hydrophobic electrolyte solvent is in the range from about 4 to about 8.

11. The method of claim 1 wherein step (c) comprises eluting the protein using an elution buffer having a pH in the range from about 2.0 to about 5.0.

12. The method of claim 2 wherein the antibody is a humanized anti-HER2 antibody.

13. The method of claim 2 wherein the antibody is a humanized anti-IgE antibody.

14. The method of claim 2 wherein the antibody is a chimeric anti-CD20 antibody.

15. The method of claim 3 wherein the immunoadhesin is a TNF receptor immunoadhesin.

* * * * *